United States Patent [19]

Sherlock

[11] 4,452,800
[45] Jun. 5, 1984

[54] SALTS OF 3(N-BUTYL)-4-HYDROXY-1-PHENYL-1,8-NAPHTHYRIDINE-2(1H)-ONE AND THEIR USE IN TREATING CHRONIC OBSTRUCTIVE LUNG DISEASES

[75] Inventor: Margaret H. Sherlock, Bloomfield, N.J.

[73] Assignee: Schering Corporation, Madison, N.J.

[21] Appl. No.: 371,623

[22] Filed: Apr. 26, 1982

[51] Int. Cl.³ .................. A61K 31/435; C07D 471/04
[52] U.S. Cl. ..................................... 424/256; 546/122
[58] Field of Search ........................ 546/122; 424/256

[56] References Cited

FOREIGN PATENT DOCUMENTS 116495 9/1977 Japan.

Primary Examiner—Henry R. Jiles
Assistant Examiner—Bernard Dentz
Attorney, Agent, or Firm—Stephen I. Miller; Gerald S. Rosen; Bruce M. Eisen

[57] ABSTRACT

There are disclosed certain alkali metal, alkaline earth metal, amine and amino acid salts of 3-(n-butyl)-4-hydroxy-1-phenyl-1,8-naphthyridine-2(1H)-one which, unlike the parent compound, are useful for orally treating chronic obstructive lung diseases such as asthma, bronchitis and the like.

30 Claims, No Drawings

SALTS OF 3(N-BUTYL)-4-HYDROXY-1-PHENYL-1,8-NAPHTHYRIDINE-2(1H)-ONE AND THEIR USE IN TREATING CHRONIC OBSTRUCTIVE LUNG DISEASES

This invention relates to certain alkali metal, alkaline earth metal, amine and amino acid salts of 3-(n-butyl)-4-hydroxy-1-phenyl-1,8-naphthyridine-2(1H)-one. More particularly, this invention relates to a compound selected from the group consisting of sodium, potassium, calcium, ethanolamine, N-methylglucamine, diethanolamine, ethylene diamine, tris hydroxymethylmethylamine and lysine salts of 3-(n-butyl)-4-hydroxy-1-phenyl-1,8-naphthyridine-2(1H)-one pharmaceutical compositions thereof and methods of treating chronic obstructive lung diseases such as asthma, bronchitis and the like therewith.

Japanese patent public disclosure (Kokai) No. 116495/77, Sept. 29, 1977 discloses various naphthyridine derivatives having significant analgesic, antiinflammatory, central nervous system depressant and diuretic effects. Among the multitude of compounds disclosed is 3-(n-butyl)-4-hydroxy-1-phenyl-1,8-naphthyridine-2(1H)-one. There is no disclosure indicating that the compounds disclosed in the Japanese publication have activity against chronic obstructive lung diseases such as asthma, bronchitis and the like and there is no disclosure of any salts of the compound.

The active compounds of this invention, are salts formed at the 4-hydroxy group of 3-(n-butyl)-4-hydroxy-1-phenyl-1, 8-naphthyridine-2(1H)-one and can be prepared as hydrates. All forms are useful for treating chronic obstructive lung diseases such as asthma, bronchitis and the like because they inhibit the release of mediators such as SRS-A (slow reacting substance of anaphylaxis) and histamine and antagonize the action of SRS-A on respiratory tissue. These chronic obstructive lung diseases can result from allergic reactions or have non-allergic causes. The compounds of this invention can thus be used to treat allergy caused diseases and their preferred use is for treating allergic chronic obstructive lung diseases. The preferred compound for this use is the sodium salt. Chronic obstructive lung disease as used herein means disease conditions in which the passage of air through the lungs is obstructed or diminished such as is the case with asthma, bronchitis and the like.

The anti-allergy activity of the active compounds is identified by tests which measure their inhibition of anaphylactic bronchospasm in sensitized guinea pigs having antigen induced SRS-A bronchoconstriction. The compounds are orally effective nonadrenergic, non-anticholinergic antianaphylactic agents. When administered orally they are active at dosages of from about 6 to 100 mg/kg of body weight; when administered parenterally, e.g. intravenously, the compounds are active at dosages of from about 1 to 10 mg/kg body weight. Surprisingly, the compounds of this invention are active in these in vivo tests whereas the parent enolic compound from which they are derived is inactive at the dosages used and is toxic when the dosage is increased in an effort to obtain practical activity.

In in vitro tests, the compounds of this invention antagonize contractions of lung parenchymal strips caused by leukotriene $C_4$. They are found to be active from these and other tests, as well as by comparison with compounds known to be effective for treating chronic obstructive lung diseases such as asthma or bronchitis. In the preferred anti-allergy use, the compounds of this invention are used to treat allergic patients by administering an anti-allergy effective amount thereof. Preferably 3-(n-butyl)-4-hydroxy-1-phenyl-1,8-naphthyridine-2(1H)-one sodium salt is administered. The allergies treated can be, for example, asthma, as well as other chronic obstructive lung diseases.

The active compounds can be administered orally, topically, parenterally, or by inhalation. The preferred mode of administration is orally.

The amount and frequency of administration will be regulated according to the judgement of the attending clinician considering such factors as age, condition and size of the patient as well as severity of the disease being treated. A typical recommended dosage regimen is oral administration of from 200 to 1500 mg/day, preferably 500 to 800 mg/day, in two to four divided doses to achieve relief of the allergic symptoms.

The compound can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal spray. Topical dosage forms can be creams, ointments, lotions and the like. Other dosage forms which can be used are transdermal devices.

The sodium and potassium salts of this invention can be readily prepared by reacting 3-(n-butyl)-4-hydroxy-1-phenyl-1,8-naphthyridine-2(1H)-one with respectively, sodium hydroxide solution or potassium hydroxide solution.

The amine and aminoacid salts can be prepared by reacting the appropriate amine or aminoacid with 3-(n-butyl)-4-hydroxy-1phenyl-1,8-naphthyridine-2(1H)-one in a compatable organic solvent.

The calcium salt can be prepared by reaction of the sodium salt with calcium chloride solution.

The following examples illustrate the preparation of the compounds of this invention as well as pharmaceutical compositions containing the compounds, all temperatures are in degrees Celsius.

EXAMPLE 1

3-(n-BUTYL)-4-HYDROXY-1-PHENYL-1,8-NAPHTHYRIDINE-2(1H)-ONE SODIUM SALT

Add 57.9 ml of 1 N sodium hydroxide aqueous solution to a stirred suspension of 17.05 g of 3-(n-butyl)-4-hydroxy-1-phenyl-1,8-naphthyridine-2(1H)-one and 140 ml of water. Stir for one hour at room temperature, cool in an ice bath and filter. Lyophilize the clear filtrate overnight to give the title compound as a monohydrate. It is a cream colored powder, m.p. 240°–260° (decomposition).

Prepare the corresponding potassium salt as a monohydrate by the process of Example 1 by replacing the sodium hydroxide aqueous solution with an equivalent amount of potassium hydroxide aqueous solution. The lyophilized potassium salt has a melting point of 215°–225°.

EXAMPLE 2

3-(n-BUTYL)-4-HYDROXY-1-PHENYL-1,8-NAPHTHYRIDINE-2(1H)-ONE ETHANOLAMINE SALT

Add 0.65 g of ethanolamine to 3-(n-butyl)-4-hydroxy-1-phenyl-1,8-naphthyridine-2(1H)-one (2.95 g.) in 100 ml of methanol. Remove the solvent in vacuo and add ethyl acetate to precipitate the title compound as a colorless salt, m.p. 228°–234°.

Prepare the following amine salts by the process of Example 2 by replacing the ethanolamine with the corresponding amine.

3-(n-Butyl)-4-hydroxy-1-phenyl-1,8-naphthyridine-2(1H)-one N-methylglucamine salt, melting point 181°–206°.

3-(n-Butyl)-4-hydroxy-1-phenyl-1,8-naphthyridine-2(1H)-one diethanolamine salt, melting point 160°–190°.

3-(n-Butyl)-4-hydroxy-1-phenyl-1,8-naphthyridine-2(1H)-one ethylenediamine salt, melting point 158°–171°.

EXAMPLE 3

3-(n-BUTYL)-4-HYDROXY-1-PHENYL-1,8-NAPHTHYRIDINE-2(1H)-ONE CALCIUM SALT

Treat a solution of 1 g (3 m moles) of the compound of Example 1 herein with 1.5 ml of 1 N calcium chloride solution (1.5 m moles). Filter the resulting cloudy solution and allow to stand until a precipitate forms. Filter and wash with acetone. Recover the title compound from water or acetone-water as a pentahydrate which is a colorless powder, m.p. >350°.

In the following examples of dosage forms, the term "Drug" represents any of the compounds prepared in the foregoing Examples 1–3.

EXAMPLE 4

| No. | Ingredient | Tablets mg/tablet | mg/tablet |
|---|---|---|---|
| 1. | Drug | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Items Nos. 1 and 2 in a suitable mixture for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

EXAMPLE 5

| No. | Ingredient | Capsules mg/tablet | mg/tablet |
|---|---|---|---|
| 1. | Drug | 100 | 500 |
| 2. | Lactose USP | 106 | 123 |
| 3. | Corn Starch, Food Grade | 40 | 70 |
| 4. | Magnesium Stearate NF | 4 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into a suitable two-piece hard gelatin capsule on a suitable encapsulating machine.

EXAMPLE 6

| Ingredient | Parenteral mg/vial | mg/vial |
|---|---|---|
| Drug Sterile Powder | 100 | 500 |

Add sterile water for injection or bacteriostatic water for injection for reconstitution.

EXAMPLE 7

| Ingredient | Injectable mg/vial | mg/vial |
|---|---|---|
| Drug | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70°.
2. Cool to 25°–35°. Charge and dissolve the sodium bisulfite, disodium edetate and sodium sulfate.
3. Charge and dissolve drug.
4. Bring the solution to final volume by adding water for injection.
5. Filter the solution through 0.22μ membrane and fill into appropriate containers.
6. Terminally sterilize the units by autoclaving.

EXAMPLE 8

| Nasal Spray | mg/ml |
|---|---|
| Drug | 10.0 |
| Phenyl Mercuric Acetate | 0.02 |
| Aminoacetic Acid USP | 3.7 |
| Sorbitol Solution | 57.0 |
| Benzalkonium Chloride Solution | 0.2 |
| Sodium Hydroxide Solution 1N to adjust pH | — |
| Water Purified USP to make | 1.0 ml |

I claim:

1. A compound selected from the group consisting of calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridine-2(1H)-one.

2. The compound of claim 1 wherein the salt is calcium.

3. The compound of claim 1 wherein the salt is ethanolamine.

4. The compound of claim 1 wherein the salt is N-methylglucamine.

5. The compound of claim 1 wherein the salt is diethanolamine.

6. The compound of claim 1 wherein the salt is ethylenediamine.

7. A compound which is physically in the form of a dry solid material, selected from the group consisting of sodium, potassium, calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridine-2(1H)-one.

8. The compound of claim 7, wherein the salt is sodium.

9. The monohydrate of the compound of claim 8.

10. The compound of claim 7 wherein the salt is potassium.

11. The compound of claim 7 wherein the salt is calcium.

12. The compound of claim 7 wherein the salt is ethanolamine.

13. The compound of claim 7 wherein the salt is N-methylglucamine.

14. The compound of claim 7 wherein the salt is diethanolamine.

15. The compound of claim 7 wherein the salt is ethylenediamine.

16. A pharmaceutical composition for treating chronic obstructive lung diseases which comprises an effective amount of a compound selected from the group consisting of sodium, sodium monohydrate, potassium, calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridine-2(1H)-one, together with a pharmaceutically acceptable carrier.

17. A pharmaceutical composition for treating allergic reactions which comprises an anti-allergy effective amount of a compound selected from the group consisting of sodium, sodium monohydrate, potassium, calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridine-2(1H)-one, together with a pharmaceutically acceptable carrier.

18. A pharmaceutical composition for treating asthma which comprises an anti-asthma effective amount of a compound selected from the group consisting of sodium, sodium monohydrate, potassium, calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridine-2(1H)-one, together with a pharmaceutically acceptable carrier.

19. A composition of claim 16 suitable for oral administration.

20. A composition of claim 17 suitable for oral administration.

21. A composition of claim 18 suitable for oral administration.

22. The composition defined in claim 16 wherein the compound is the sodium salt of 3-(n-butyl)-4-hydroxy-1-phenyl-1,8-naphthyridin-2-(1H)-one.

23. The composition defined in claim 17 wherein the compound is the sodium salt of 3-(n-butyl)-4-hydroxy-1-phenyl-1,8-naphthyridin-2(1H)-one.

24. The composition defined in claim 18 wherein the compound is the sodium salt of 3-(n-butyl)-4-hydroxy-1-phenyl-1,8-naphthyridin-2(1H)-one.

25. A method of treating chronic obstructive lung diseases which comprises administering an effective amount of a compound selected from the group consisting of sodium, sodium monohydrate, potassium, calcium, ethanolamine, N-methylglucamine, diethanolamine, ethylenediamine, trishydroxyethyl-methylamine and lysine salts of 3-(n-butyl)-4-hydroxy-1-phenyl-1,8-naphthyridin-2-(1H)-one to a patient having said disease.

26. A method of treating allergic diseases which comprises administering an anti-allergy effective amount of a compound selected from the group consisting of sodium, sodium monohydrate, potassium, calcium, ethanolamine, N-methyl-glucamine, diethanolamine, ethylenediamine, trishydroxyethyl-methylamine and lysine salts of 3-(n-butyl)-4-hydroxy-1-phenyl-1,8-naphthyridin-2(1H)-one to a patient having an allergic disease.

27. A method of treating asthma which comprises administering an anti-asthma effective amount of a compound selected from the group consisting of sodium, sodium monohydrate, potassium, calcium, ethanolamine, N-methyl-glucamine, diethanolamine, ethylenediamine, trishydroxyethyl-methylamine and lysine salts of 3-(n-butyl)-4-hydroxy-1-phenyl-1,8-naphthyridin-2(1H)-one to a patient having asthma.

28. The method defined in claim 25 wherein the compound is the sodium salt of 3-(n-butyl)-4-hydroxy-1-phenyl-1,8-naphthyridin-2(1H)-one.

29. The method defined in claim 26 wherein the compound is the sodium salt of 3-(n-butyl)-4-hydroxy-1-phenyl-1,8-naphthyridin-2(1H)-one.

30. The method defined in claim 27 wherein the compound is the sodium salt of 3-(n-butyl)-4-hydroxy-1-phenyl-1,8-naphthyridin-2(1H)-one.

* * * * *